United States Patent
Katoh et al.

(10) Patent No.: US 6,656,303 B1
(45) Date of Patent: Dec. 2, 2003

(54) PROCESS FOR PRODUCING SHEET FOR SUSTAINEDLY RELEASING VOLATILE DRUG

(75) Inventors: Kazuya Katoh, Tokyo (JP); Yuichi Mizukami, Osaka (JP)

(73) Assignee: Carex, Inc., Osaka (JP)

( * ) Notice: Subject to any disclaimer, the term of this patent is extended or adjusted under 35 U.S.C. 154(b) by 0 days.

(21) Appl. No.: 09/926,708
(22) PCT Filed: Jun. 2, 2000
(86) PCT No.: PCT/JP00/03583

§ 371 (c)(1),
(2), (4) Date: Dec. 5, 2001

(87) PCT Pub. No.: WO00/74737

PCT Pub. Date: Dec. 14, 2000

(30) Foreign Application Priority Data

Jun. 7, 1999 (JP) ............................................ 11-159348

(51) Int. Cl.$^7$ .............................. B32B 31/00; C09J 5/00
(52) U.S. Cl. ........................ 156/182; 424/405; 424/443; 424/76.8
(58) Field of Search ................................ 156/145, 146, 156/182; 424/404, 407, 409, 411, 419, 448, 500, 501, 76.8, 77, 484, 443

(56) References Cited

U.S. PATENT DOCUMENTS 5,554,376 A * 9/1996 Sekiyama et al. ........... 424/404

FOREIGN PATENT DOCUMENTS

| EP | 0 888 712 A1 | | 1/1999 | |
|---|---|---|---|---|
| JP | 10-94593 | | 4/1998 | |
| JP | 1094593 | * | 4/1998 | ............. A61L/9/04 |
| JP | 10-217381 | | 8/1998 | |
| JP | 11130609 | * | 5/1999 | .......... A01N/47/48 |
| WO | WO98/23159 | | 6/1998 | |

* cited by examiner

Primary Examiner—Richard Crispino
Assistant Examiner—Chan Sing B
(74) Attorney, Agent, or Firm—Armstrong, Kratz, Quintos, Hanson & Brooks, LLP

(57) ABSTRACT

A process for producing a sheet for sustained release of a volatile drug, characterized by dissolving a resin serving as an adhesive in a volatile drug and using the resultant solution as a coating fluid to bond a film permeable to the volatile drug to another film permeable or impermeable to the volatile drug. No organic solvent or peeling film for process is used, accordingly, unlike the so far known process. Consequently, it is not necessary to provide the drying step for removing an organic solvent as well as any thermal energy. As a result, the number of production steps can be reduced considerably. In addition, since the volatile drug is homogeneously diluted in the adhesive, the volatile drug can be incorporated accurately and evenly even in an amount as small as 1 g/m$^2$ or less. According to the process of the invention, a thinner layer containing a volatile drug can be formed.

5 Claims, No Drawings

PROCESS FOR PRODUCING SHEET FOR SUSTAINEDLY RELEASING VOLATILE DRUG

TECHNICAL FIELD

The present invention relates to a process for producing sheets for sustained release of volatile drugs which are used as perfumes, fungicides, antiseptics, insect repellents or insecticides, bactericides, antimicrobials, rust preventives, and the like.

BACKGROUND ART

It is known that one of volatile drugs, isothiocyanic acid ester which is contained in mustard or Japanese horse raddish, has a bacteriostatic and bactericidal action at an extremely low vapor concentration as low as several ppm to several ten ppm whether they are natural products or synthetic ones.

In a known process for producing sheets for sustained release of volatile drugs, as disclosed in Japanese Unexamined Patent Publication Nos. 6-212136/1994 and 7-24048/1995, a pressure-sensitive adhesive layer is formed on a film, which is then impregnated with a volatile drug, and on which another film is stuck.

In the above-described process, however, it is necessary to provide a step for forming a pressure-sensitive adhesive layer on a film in advance. In order to form a pressure-sensitive adhesive layer, an organic solvent has to be used to dissolve a pressure-sensitive adhesive. Moreover, since the pressure-sensitive adhesive is dissolved in an organic solvent and then applied on a film, an additional drying step requiring thermal energy is necessary thereafter to remove the organic solvent. In addition, in the course of the production, until impregnation of the volatile drug, a peeling film for protecting the pressure-sensitive adhesive layer is required. Further, if the pressure-sensitive adhesive layer is formed with a preliminarily prepared mixture of a pressure-sensitive adhesive and a volatile drug, the latter would be lost by vaporization during the drying step. In the above-mentioned process for impregnating the pressure-sensitive adhesive layer with a volatile drug, it is advantageous that the drug can be retained effectively in the adhesive layer in high concentration. The process, however, is not so desirable in the recent situation that improvement and protection of the global environment have strongly been protested because it is necessary to use an organic solvent, thermal energy and a peeling film for process through a number of steps.

In sheets for sustained release of volatile drugs utilized on an industrial scale, if the drugs are contained unevenly in the sheets, they might act locally and undesirably. In order to bring out a uniform effect on the part to be treated, the volatile drug has to be distributed evenly on the whole sheet. If the volatile drug can be distributed evenly on the whole sheet, it would be favorable since the content of the volatile drug could be made proportional to the size of the sheet.

When a sheet for sustained release of an isothiocyanic acid ester is placed in a lunch box to expect a bacteriostatic and bactericidal action, it is desirous to make a very minute amount of isothiocyanic acid ester release from the sheet. Thus, it is possible to maintain the vapor concentration of isothiocyanic acid ester in the lunch box at several ppm to several ten ppm.

In view of the above situation, the purpose of the invention is to provide a process for producing sheets for sustained release of volatile drugs, in which the volatile drugs can be incorporated conveniently, accurately and evenly in the sheets without using any organic solvent, thermal energy and any peeling film for process as used in the so far known process.

DISCLOSURE OF THE INVENTION

The present inventors repeatedly examined in various ways, and as a result they found that a solution which was prepared by dissolving a variety of resins serving as adhesives, e.g., a pressure-sensitive adhesive, solvent-type adhesive, reaction-type adhesive, and the like in a desired volatile drug, could be used as a coating fluid to bond a film permeable to the volatile drug to another film permeable or impermeable to the volatile drug. Thus, a sustained release sheet which is contained a volatile drug accurately and evenly could conveniently be produced without using any organic solvent, thermal energy and any peeling film for process as used in the so far known process.

The present invention was completed based on these findings. The process of the invention for producing a sheet for sustained release of a volatile drug comprises dissolving a resin serving as an adhesive in a volatile drug and applying the resulting solution on a film impermeable to the volatile drug, followed by sticking another film permeable to the volatile drug on the applied surface.

In another embodiment of the invention, the process for producing a sheet for sustained release of a volatile drug comprises dissolving a resin serving as an adhesive in a volatile drug and applying the resulting solution on a film permeable to the volatile drug, followed by sticking another film permeable or impermeable to the volatile drug on the applied surface.

In another embodiment of the invention, the process for producing a sheet for sustained release of a volatile drug is characterized in that the above-described volatile drug is an isothiocyanic acid ester.

BEST MODE FOR CARRYING OUT THE INVENTION

In the invention, the film impermeable to volatile drugs to be used may properly be selected from a variety of films to which the volatile drugs are impermeable, including for example resin films such as vinylidene, acrylonitrile, ethylene-polyvinyl alcohol copolymer, polyethylene terephthalate, polyamide, polycarbonate, and the like, the resin films metal-vaporized, metallic foils, and their complexes. The films may be of 10 $\mu$m–100 $\mu$m, preferably 20 $\mu$m–50 $\mu$m in thickness.

In the invention, the film permeable to volatile drugs to be used may properly be selected from a variety of films to which the volatile drugs are permeable, including for example polyolefin-type resins such as polyethylene and polypropylene, biodegradable resins such as poly-lactic acid, resin films such as vinyl chloride, paper, cloth, synthetic paper and their complexes. The films may be of 5 $\mu$m–200 $\mu$m, preferably 10 $\mu$m–100 $\mu$m in thickness.

In order to prevent release of the volatile drug before use of the sustained release sheet, it is possible to use a film permeable to the volatile drug on which a protective film composed of a film impermeable to the volatile drug has been laminated so as to be freely peeled off, whereby a solution prepared by dissolving the resin serving as an adhesive in the volatile drug is applied on the backside of the laminated protective film, to which a film impermeable to the volatile drug is stuck.

The volatile drug applicable to the invention includes, for example, natural perfumes such as animal perfumes such as musk, civet (from civet gland), castor (beaver perfume), ambergris (from the sperm whale), etc., plant perfumes composed of plant essential oils such as lavender oil, peppermint oil, lemon oil, orange oil, rose oil, camphor oil, sandalwood oil, cypress oil, etc., synthetic perfumes composed of terpene compounds, ester compounds, aromatic compounds, etc., or their composite perfumes; isothiocyanic acid esters such as methyl isothiocyanate, ethyl isothiocyanate, allyl isothiocyanate, isobutyl isothiocyanate, n-butyl isothiocyanate, phenyl isothiocyanate, benzyl isothiocyanate, etc.; fungicides such as 3-methyl-4-isopropylphenol; insect repellents or insecticides such as DDVP, anethole, propetamphos, piperonyl butoxide, etc.; antiseptics such as creosote oil; and the like. In this invention, however, since a resin serving as an adhesive has to be dissolved in a volatile drug, the latter per se has to be liquid at ordinary temperature or, when dissolved in another liquid volatile drug, be in a liquid state to dissolve the resin serving as an adhesive.

The resin which is used as an adhesive in the invention, in relation to the desired volatile drug, may properly be selected from those soluble in the volatile drugs, for example, acrylic resins such as copolymers of one or more of (meth)acrylic acid esters such as n-butyl (meth)acrylate, hexyl (meth)acrylate, 2-diethylbutyl (meth)acrylate, isooctyl (meth)acrylate, 2-methoxyethyl (meth)acrylate, 2-ethylhexyl (meth)acrylate, decyl (meth)acrylate, dodecyl (meth)acrylate, tridecyl (meth)acrylate, and the like, with a functional monomer copolymerizable with said esters, such as (meth)acrylic acid, itaconic acid, maleic acid, maleic anhydride, hydroxyethyl acrylate, hydroxypropyl acrylate, acrylamide, dimethylacrylamide, methylaminoethyl methacrylate, and the like; vinyl-type resins such as ethyl vinyl ether, propyl vinyl ether, butyl vinyl ether, 2-ethylhexyl vinyl ether, and the like; vinyl acetate resins; polyimide resins; polyester resins; rubber-type resins such as natural rubber or synthetic rubber such as styrene-isoprene-styrene block copolymer, styrene-butadiene block copolymer, styrene-butadiene-styrene block copolymer, isoprene rubber, polybutene rubber, butyl rubber, and the like; epoxy resins; cyanoacrylate resins; urethane acrylate resins; polyester acrylate resins; urethane resins; and the like, which are utilizable as a variety of adhesives such as pressure-sensitive adhesives, solvent-type adhesives, reaction-type adhesives, and the like.

The resin serving as an adhesive may be used in combination with an agent for giving cohesiveness such as terpene resin, petroleum resin, and the like; a regulator for cohesive force and retention such as liquid paraffin, animal and vegetable oils (e.g., olive oil, soybean oil, beef tallow, lard), polybutene, lower isoprene, wax, and the like; a filler such as titanium oxide, zinc oxide, aluminum metasilicate, calciumu carbonate, calcium phosphate, and the like. These agents may preliminarily be combined with a resin serving as an adhesive prior to or at the same time in dissolution.

Moreover, as a resin serving as an adhesive other than the above-mentioned ones, any kind of resins which are soluble in the volatile drugs can also be used.

The mixing ratio of the volatile drug may preferably be 5% to 90%, more preferably 20% to 60% for the whole solution by weight. The reason is that when the ratio of the volatile drug is less than 5%, the volatile drug may possibly be retained in the sheet without being released, and if it is over 90%, sufficient adhesion force possibly could not be obtained for two films.

When a film permeable to a volatile drug is stuck on another film permeable or impermeable to the volatile drug using a solution prepared by dissolving a resin serving as an adhesive in the volatile drug as a coating fluid, the volatile drug in the coating fluid is distributed into the film permeable to the volatile drug. As a result, the concentration of the volatile drug in the coating fluid is decreased, while the concentration of the resin is increased. The coating fluid in a liquid state is converted into a viscous fluid, which is further converted into an elastic body (a solid in some cases). Thus, the resin becomes an adhesive that has a sufficient force to adhere two films.

EXAMPLES

The following examples illustrate in detail the process of the invention for producing sheets for sustained release of volatile drugs.

Example 1

In 735 g of allyl isothiocyanate was dissolved 600 g of terpene hydrogenated resin (Yasuhara Chemical Co., Ltd.; "Clearon M-115") and 300 g of styrene-isoprene-styrene block copolymer resin (Shell Japan Co.; "Kraton D-1107CP") with stirring.

The resulting solution was applied on a film impermeable to the volatile drug, i.e., polyethylene terephthalate film (Toray Industries Inc.; "Lumirror T-61") of 25 $\mu$m in thickness at a rate of 1.8 g/m$^2$ using a wet laminator. Then, a film permeable to the volatile drug, i.e., polyethylene film (Futamura Chemical Industries Co., Ltd.; "Taiko FL-XMTN") of 30 $\mu$m in thickness was stuck on the applied surface to give a sheet containing about 800 mg/m$^2$ of allyl isothiocyanate.

The resulting sheet was rolled up and allowed to stand for 10 minutes, and the strength of adhesion between the polyethylene terephthalate film and the polyethylene film was confirmed to be 80 g/25 mm or more, which was sufficient for adhesion. It was considered that this strength might be caused by diffusion of allyl isothiocyanate into the permeable film, i.e., polyethylene film. The thickness of the adhesive layer was about 1.0 $\mu$m.

Example 2

In 300 g of allyl isothiocyanate was dissolved 389 g of an isocyanate for a reaction-type polyurethane adhesive (Dainichiseika Color & Chemicals Mfg. Co., Ltd.; "Nonsolbond XC-235") and 311 g of a polyol for a reaction-type polyurethane adhesive (Dainichiseika Color & Chemicals Mfg. Co., Ltd.; "Nonsolbond XA-129") with well stirring to give a homogeneous compound.

The resulting solution was applied on a film permeable to the volatile drug, i.e., polypropylene film (Futamura Chemical Industries Co., Ltd.; "Taiko FC-FHMK") of 30 $\mu$m in thickness at a rate of 1.6 g/m$^2$ using a wet laminator. The same film was stuck on the applied surface to give a sheet containing about 480 mg/m$^2$ of allyl isothiocyanate.

The resulting sheet was rolled up and allowed to stand for 60 minutes, and the strength of adhesion of the polypropylene films was confirmed to be 800 g/25 mm or more, which was sufficient for adhesion. The thickness of the adhesive layer was about 1.1 $\mu$m.

Example 3

In 900 g of allyl isothiocyanate was dissolved 600 g of terpene hydrogenated resin (Yasuhara Chemical Co., Ltd.;

"Clearon M-115") and 300 g of styrene-isoprene-styrene block copolymer resin (Shell Japan Co.; "Kraton D-1107CP") with stirring.

The resulting solution was applied on a film permeable to the volatile drug, i.e., polypropylene film (Futamura Chemical Industries Co., Ltd.; "Taiko FC-FHMK") of 30 μm in thickness at a rate of 2.0 g/m² using a wet laminator. Then, a film impermeable to the volatile drug, i.e., polyethylene terephthalate film (Toray Industries Inc.; "Lumirror T-61") of 38 μm in thickness was stuck on the applied surface to give a sheet containing about 1000 mg/m² of allyl isothiocyanate.

The resulting sheet was rolled up and allowed to stand for 15 minutes, and the strength of adhesion between the polypropylene film and the polyethylene terephthalate film was confirmed to be 80 g/25 mm or more, which was sufficient for adhesion. The thickness of the adhesive layer was about 1.0 μm.

INDUSTRIAL APPLICABILITY

In the production process of the invention, a solution which is prepared by dissolving a resin serving as an adhesive in a volatile drug is used as a coating fluid to bond a film permeable to the volatile drug to another film permeable or impermeable to the volatile drug. No organic solvent or peeling film for process is used, accordingly, unlike the so far known process. Consequently, it is not necessary to provide the drying step for removing an organic solvent as well as any thermal energy. As a result, the number of production steps can be reduced considerably. In addition, since the volatile drug is homogeneously diluted in the adhesive, the volatile drug can be incorporated accurately and evenly even in an amount as small as 1 g/m² or less. According to the process of the invention, a thinner layer containing a volatile drug can be formed.

What is claimed is:

1. A process for producing a sheet for sustained release of a volatile drug which comprises dissolving a resin serving as an adhesive in a volatile drug and applying the resulting solution on a film impermeable to the volatile drug, followed by sticking another film permeable to the volatile drug on the applied surface.

2. A process for producing a sheet for sustained release of a volatile drug which comprises dissolving a resin serving as an adhesive in a volatile drug and applying the resulting solution on a film permeable to the volatile drug, followed by sticking another film permeable or impermeable to the volatile drug on the applied surface.

3. A process for producing a sheet for sustained release of a volatile drug as claimed in claim 1 or 2, wherein the above-described volatile drug is an isothiocyanic acid ester.

4. A process for producing a sheet for sustained release of a volatile drug as claimed in claim 1 or 2, wherein the volatile drug is liquid at room temperature.

5. A process for producing a sheet for sustained release of a volatile drug as claimed in claim 1 or 2, wherein the volatile drug is in a liquid state when dissolved in another liquid volatile drug so as to dissolve said resin serving as an adhesive.

* * * * *